(12) United States Patent
Tabor et al.

(10) Patent No.: US 7,341,087 B2
(45) Date of Patent: Mar. 11, 2008

(54) APPARATUS FOR APPLYING DISCRETE PARTS TO A MOVING WEB

(75) Inventors: Jeffery Tabor, Appleton, WI (US); Willard Hawley, Seymour, WI (US); John Flannery, Shiocton, WI (US); Michael Schrlau, Drexel Hill, PA (US); Steven Schapel, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 1117 days.

(21) Appl. No.: 10/038,766

(22) Filed: Jan. 2, 2002

(65) Prior Publication Data

US 2003/0121614 A1 Jul. 3, 2003

(51) Int. Cl.
*B32B 37/00* (2006.01)

(52) U.S. Cl. .................. 156/538; 156/552; 156/553; 156/556; 269/21

(58) Field of Classification Search .............. 156/552, 156/553, 519, 164, 214, 230, 556, 557, 285, 156/538, 539, 555, 566, 567, 568, 582; 198/377.08; 269/21

See application file for complete search history.

(56) References Cited

U.S. PATENT DOCUMENTS

| | | | |
|---|---|---|---|
| 3,847,273 A | 11/1974 | Buhayar | |
| 3,847,710 A * | 11/1974 | Blomqvist et al. | 156/511 |
| 4,081,301 A * | 3/1978 | Buell | 156/164 |
| 4,394,898 A | 7/1983 | Campbell | |
| 4,394,933 A | 7/1983 | Ackley | |
| 4,578,133 A * | 3/1986 | Oshefsky et al. | 156/164 |
| 4,608,115 A * | 8/1986 | Schroth et al. | 156/519 |
| 4,617,082 A | 10/1986 | Oshefsky et al. | |
| 4,726,873 A | 2/1988 | Ales et al. | |
| 4,726,876 A | 2/1988 | Tomsovic, Jr. | |
| 4,941,939 A | 7/1990 | Nomura et al. | |
| 4,943,340 A * | 7/1990 | Ujimoto et al. | 156/496 |
| 5,014,395 A | 5/1991 | Stäheli et al. | |
| 5,025,910 A | 6/1991 | Lasure et al. | |
| 5,104,116 A | 4/1992 | Pohjola | |
| 5,224,405 A | 7/1993 | Pohjola | |
| 5,244,530 A | 9/1993 | Collins et al. | |
| 5,291,692 A * | 3/1994 | Takahashi et al. | 451/388 |
| 5,660,665 A | 8/1997 | Jalonen | |
| 5,716,478 A | 2/1998 | Boothe et al. | |
| 5,725,734 A | 3/1998 | Herman et al. | |

(Continued)

FOREIGN PATENT DOCUMENTS

GB 942214 * 11/1963

(Continued)

*Primary Examiner*—James Sells
(74) *Attorney, Agent, or Firm*—Brinks Hofer Gilson & Lione

(57) ABSTRACT

An apparatus and method for engaging and transferring a discrete part having a varying thickness to a substrate web. The apparatus includes one or more transfer assemblies and a web conveyor supporting the substrate web. Each transfer assembly includes a carrier member adapted to engage and transport the discrete part. One of the carrier member and the web conveyor includes a recessed portion for receiving portions of the discrete part that are relatively thicker than other portions of the discrete part, thereby ensuring more uniform contact between the discrete part and the web substrate.

19 Claims, 8 Drawing Sheets

U.S. PATENT DOCUMENTS

| | | |
|---|---|---|
| 5,759,340 A | 6/1998 | Boothe et al. |
| 5,830,296 A * | 11/1998 | Emenaker et al. .......... 156/219 |
| 5,853,530 A | 12/1998 | Allen |
| 5,935,363 A | 8/1999 | Gilman et al. |
| 6,074,333 A | 6/2000 | Rajala et al. |
| 6,098,249 A | 8/2000 | Toney et al. |
| 6,116,317 A | 9/2000 | Tharpe, Jr. et al. |
| 6,139,004 A | 10/2000 | Couillard et al. |
| 6,319,342 B1 * | 11/2001 | Riddell ...................... 156/62.4 |
| 6,482,278 B1 * | 11/2002 | McCabe et al. ........... 156/73.1 |
| 6,620,276 B1 * | 9/2003 | Kuntze et al. .............. 156/164 |

FOREIGN PATENT DOCUMENTS

| | | |
|---|---|---|
| WO | WO 01/66450 A2 | 9/2001 |
| WO | WO 01/66453 A2 | 9/2001 |

* cited by examiner

APPARATUS FOR APPLYING DISCRETE PARTS TO A MOVING WEB

FIELD OF THE INVENTION

The present invention relates generally to an apparatus and method for receiving discrete parts traveling at a first speed and applying the parts to a web traveling at a different speed. The invention more particularly concerns an apparatus and method for receiving a discrete part having a varying thickness and traveling at a certain speed and applying the discrete part onto a substrate web traveling at a different speed.

BACKGROUND

Absorbent products, such as disposable diapers or incontinence inserts, generally have been manufactured by a process where discrete parts or components, such as absorbent materials, leg elastics, waist elastics, tapes, and other fasteners such as hook and loop materials or snaps, have been applied to a continuously moving web. Often, the speed at which the parts are fed into the process is not the same as the speed of the product web itself is traveling. Thus, the speed of the parts must be changed to match the speed of the product web to properly apply the parts without adversely affecting the process or the finished discrete parts.

A prior apparatus for applying discrete parts to a moving web is disclosed is in U.S. Pat. Nos. 5,716,478 and 5,759,340, both issued to Boothe et al. The apparatus includes a mechanism for severing a first substrate web traveling at a first speed into discrete parts and applying the discrete parts onto a second substrate web traveling at a second speed. The apparatus includes at least one transfer assembly which is configured to rotate about a first axis. The transfer assembly includes an outer surface which is configured to receive the discrete parts and apply the discrete parts to the second substrate web. The apparatus also includes a drive member which is configured to rotate about a second axis which is offset from the first axis of the transfer assembly. At least one coupler arm is pivotally connected to the drive member about a pivot point located radially outward from the second axis. The coupler arm includes a cam end which is configured to follow a predetermined curvilinear path and a crank end which is slidably connected to the transfer assembly. A drive mechanism is configured to rotate the drive member about the second axis. As the drive member is rotated, the cam end of the coupler arm is guided along the curvilinear path and the crank end of the coupler arm slidably engages the transfer assembly thereby pivoting the coupler arm about the pivot point to vary an effective drive radius of the transfer assembly and rotate the transfer assembly at a variable speed. In use, the transfer assembly is configured to maintain a substantially constant first surface speed as the discrete parts are received and a substantially constant second surface speed as the discrete parts are applied to the second substrate web.

Although the apparatus disclosed in the Boothe et al. patents has shown to be very effective in applying discrete parts to a moving web, one problem arises in transferring discrete parts having a varying thickness. When discrete parts having a varying thickness are used, the discrete part may only be placed in contact with the moving web at the thickness portion of the discrete part. This may lead to less than optimal performance in transferring and securing the discrete part to the moving web, and may result in decreased equipment reliability.

Accordingly, there remains a need in the art for an apparatus that can effectively transfer a discrete part having a varying thickness to a moving web.

SUMMARY

The present invention provides an improved apparatus and method for transferring a discrete part having a varying thickness to a substrate web. In one aspect of the invention, a transfer assembly having a carrier member is provided. The carrier member includes a carrier body having a discrete part engaging outer surface. The outer surface has a generally convex top portion and a generally convex recessed portion spaced inwardly from the top surface. The top portion is adapted and configured to engage a first portion of a discrete part having a first thickness. The recessed portion is adapted and configured to engage at least one portion of the discrete part having at least one thickness greater the first thickness.

According to another aspect of the present invention, an apparatus for applying discrete parts onto a substrate web includes a web conveyor and one or more transfer assemblies. The web conveyor is adapted to support and advance a substrate web. The one or more transfer assemblies are configured to rotate about an axis. Each transfer assembly includes an outer surface configured to engage a discrete part. The outer surface of the transfer assembly is spaced from the web conveyor such that the discrete part may be applied to the substrate web. The outer surface includes one or more recessed portions for engaging at least one portion of the discrete part that is relatively thicker than other portions of the discrete part.

In another aspect of the invention, an apparatus having one more transfer assemblies and a web conveyor are provided. The one or more transfer assemblies are configured to rotate about an axis. Each of the transfer assemblies includes an outer surface configured to engage the discrete parts. The web conveyor is spaced from the outer surface of one of the transfer assemblies. The web conveyor has an outer surface adapted to support and advance a substrate web, and the outer surface of the web conveyor includes at least one recessed portion for engaging at least one portion of each of the discrete parts that is relatively thicker than other portions of the discrete parts.

According to yet another aspect of the present invention, an apparatus for applying discrete parts having a varying thickness onto a substrate web traveling at a second speed is provided. The apparatus includes a web conveyor, one or more transfer assemblies, a drive member, at least one coupler arm, and a drive mechanism. The web conveyor is adapted to support and advance a substrate web. The one or more transfer assemblies are configured to rotate about a first axis. The one or more transfer assemblies includes an outer surface which is configured to transport the discrete parts and apply the discrete parts to the substrate web. The outer surface includes at least one recessed portion for engaging at least one portion of the discrete parts that is relatively thicker than other portions of the discrete parts. The drive member is configured to rotate about a second axis which is offset from the first axis of the transfer assembly. The coupler arm(s) are pivotally connected to the drive member about a pivot point, the coupler arm including a cam end which is configured to follow a curvilinear path and a crank end which is slidably connected to the transfer assembly. The drive mechanism is adapted to rotate the drive member about the second axis wherein, as the drive member is rotated, the cam end of the coupler arm is guided along the curvilinear path and the crank end of the coupler arm slidably engages the transfer assembly thereby pivoting the coupler arm about the pivot point to vary an effective drive radius of the transfer assembly and rotate the transfer assembly at a variable speed.

Those skilled in the art will recognize other aspects of the present invention in view of the detailed description and claims that follow.

BRIEF DESCRIPTION OF THE DRAWINGS

The present invention will be more fully understood and further advantages will become apparent when reference is made to the following detailed description of the invention and the accompanying figures wherein like numerals represent like elements. The figures are merely representative and are not intended to limit the scope of the appended claims.

DETAILED DESCRIPTION OF THE PREFERRED EMBODIMENTS

The present invention provides a carrier member and a transfer assembly for applying discrete parts having a varying thickness to a substrate web. Moreover, the present invention provides a transport apparatus and method for receiving discrete parts traveling at a first speed and applying the parts to a substrate web traveling at a second speed. The carrier member, the transfer assembly, the transport apparatus and the method are particularly useful for receiving discrete parts such as absorbent layers or leg or waist elastics, and applying the parts to a substrate web to form a product web of interconnected disposable absorbent articles such as, for example, disposable diapers or incontinence inserts.

Figure 1:
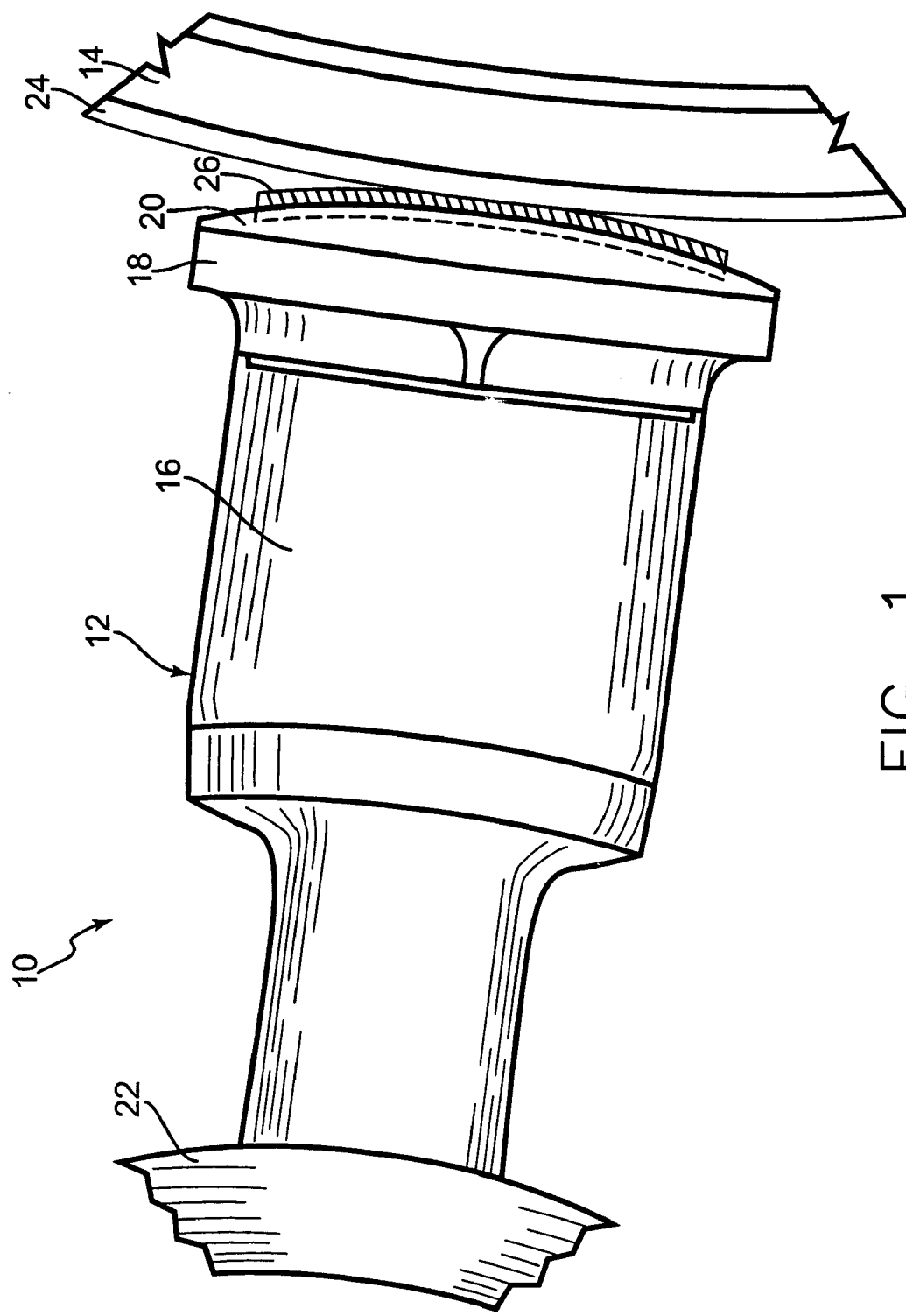
FIG. 1 is a front view of a transport apparatus according to one aspect of the present invention.

Referring now to FIG. 1, a transport apparatus is shown generally at 10. The transport apparatus 10 includes transfer assembly 12 and a web conveyor 14. The transfer assembly 12 includes a support member 16 attached at one end to a carrier base 18, which in turn supports a carrier member 20. The other end of the support member 16 is connected with a drive member 22 which is configured to move the transfer assembly 12 through a range of motion in a generally curvilinear path. Those skilled in the art will recognize the conventional drive members 22 that may be used with to rotate the transfer assembly 12. The web conveyor 14 is adapted to support and advance a substrate web 24. In the preferred embodiment shown, the web conveyor 14 is in the form of a rotary drum, however, in alternate embodiments, the web conveyor 14 may take the form of a roller, a linear conveyor, or other forms that will be apparent to those skilled in the art.

The transport apparatus 10 is designed to engage a discrete part 26, transport the discrete part 26 through the curvilinear path, and apply the discrete part 26 to the substrate web 24. The discrete parts 26 and the substrate web 24 together form at least a portion of a product. Those skilled in the art will recognize that the transport device 10 may be used with many types of discrete parts that may be used for constructing a variety of products, as will become apparent from the description that follows. In preferred embodiments of a method according to one aspect of the invention, the transport device 10 is used to form disposable absorbent articles, such as diapers, training pants, or incontinence inserts.

Figure 2:
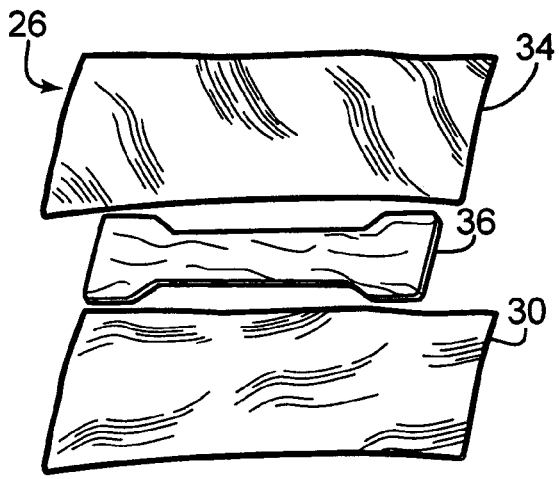
FIG. 2 is an exploded perspective view of a discrete part used in a method of making an absorbent product in accordance with the present invention.
Figure 3:
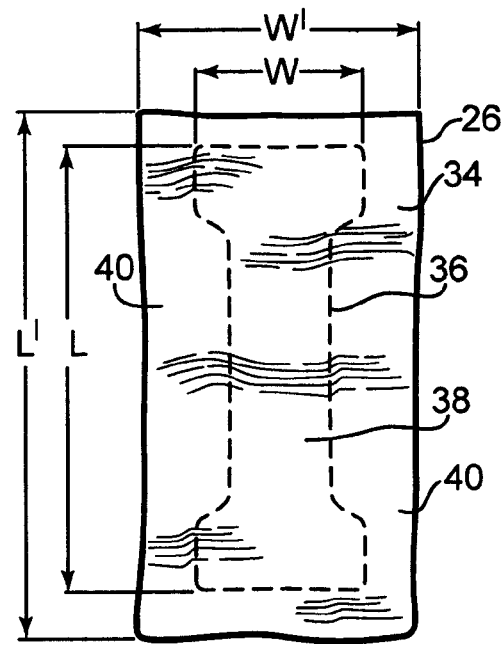
FIG. 3 is a top view of the discrete part of FIG. 3.
Figure 4:
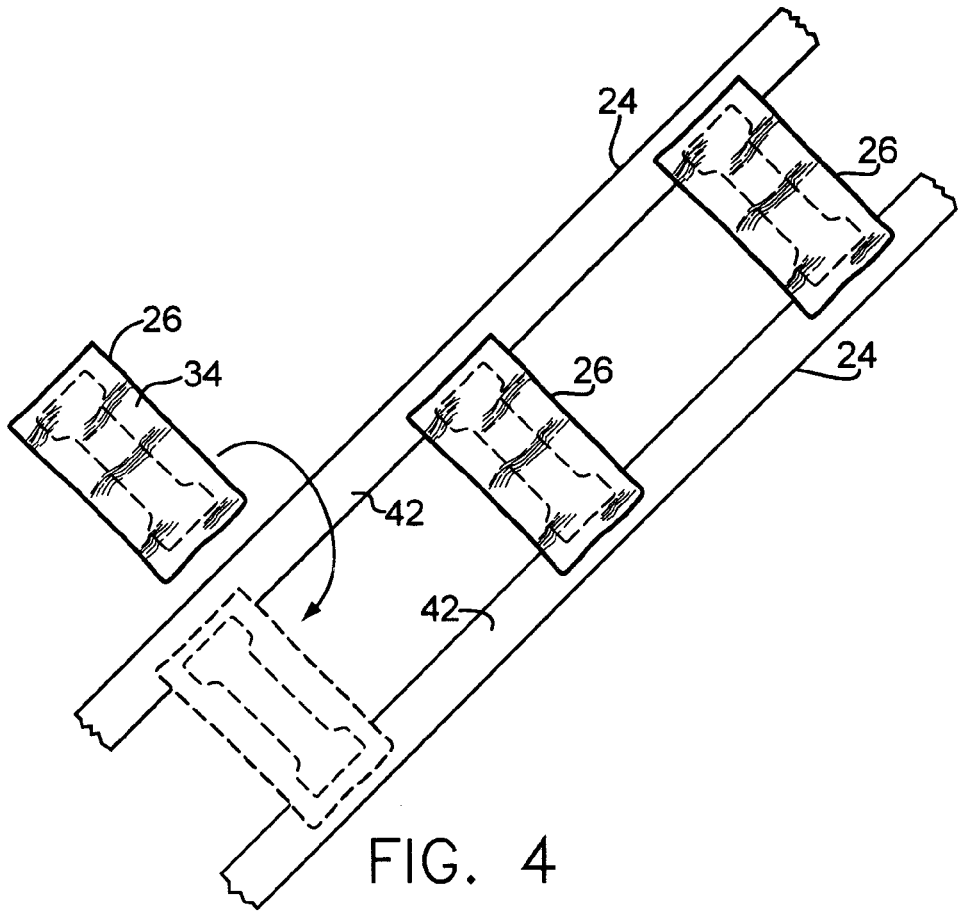
FIG. 4 illustrates a method of making an absorbent product using the discrete part of FIGS. 2 and 3.

An example of a process for forming an absorbent product is shown representatively in FIGS. 2-4. As shown in FIG. 2, the discrete part 26 is shown as a multi-layered article including a fluid impermeable layer 30, a body-side liner 34, and an absorbent layer 36 sandwiched between the fluid impermeable layer 30 and the liner 34. The materials used to make such layers may be any of those conventional materials known in the art. Because the absorbent layer 36 has length L and width W that are smaller than the overall length L' and width W', respectively, of the discrete part 26, the area of the discrete part 26 having the absorbent layer 36 defines a portion 38 (FIG. 3) of the discrete part 26 that is thicker relative to the other portions 40 of the discrete part 26.

Referring now to FIG. 4, the discrete part 26 is placed upon an outward surface 42 of the substrate web 24 by the transfer assembly 12 (FIG. 1). The discrete parts 26 are sequentially placed onto the substrate web 24 one after another as the substrate web 24 is advanced by the web conveyor 14. In the preferred embodiment shown in FIG. 4, the substrate web is shown as a pair of webs, however, those skilled in the art will appreciate that the web 24 could be formed as a single web, or multiple webs.

Figure 5A:
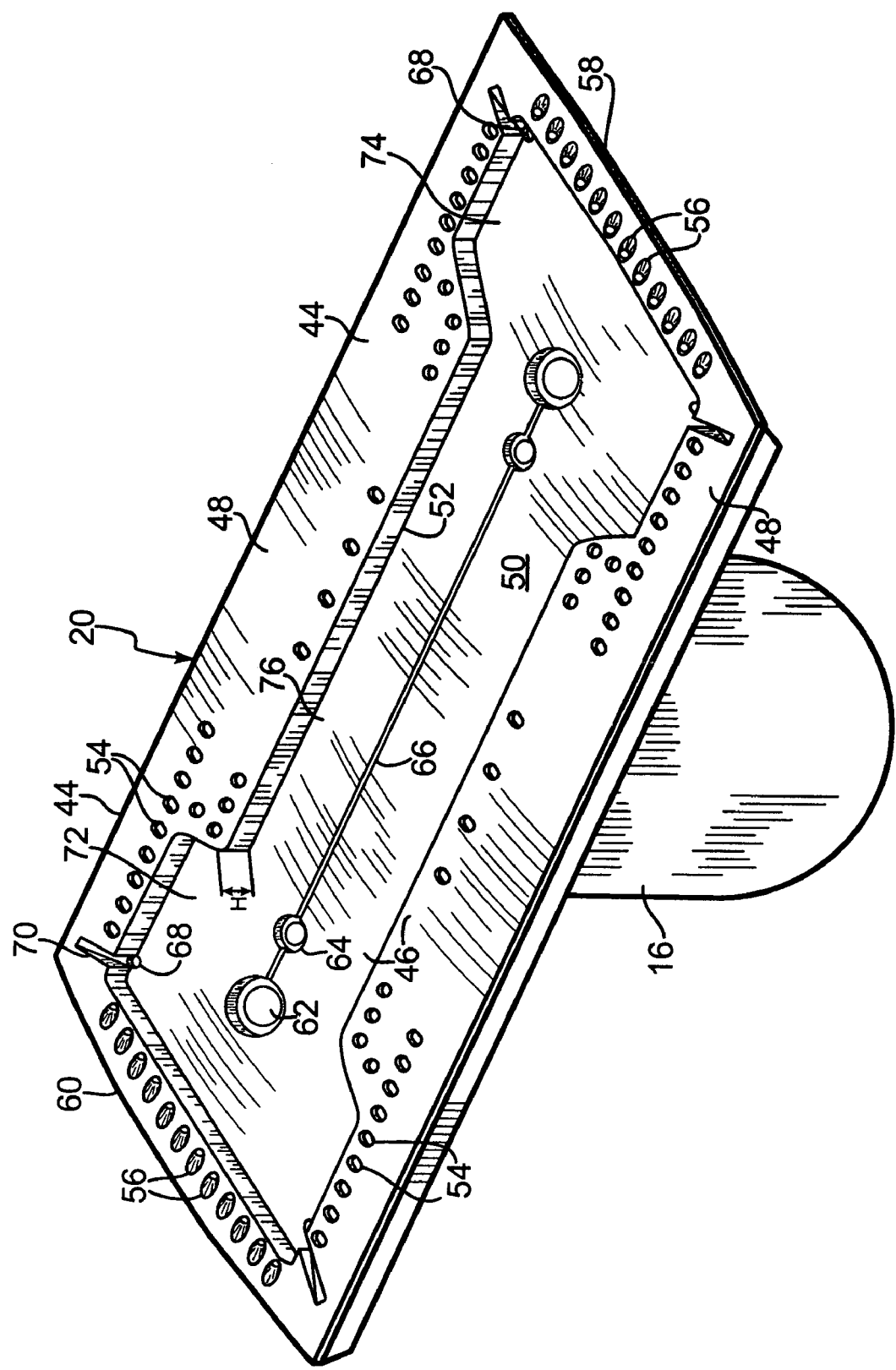
FIG. 5A is a perspective view of a transfer assembly in accordance with another aspect of the invention.

FIG. 5A illustrates one embodiment of the transfer assembly 12, and more specifically, of the carrier member 20, according to an aspect of the present invention. The carrier member 20 is preferably formed from an elongated, unitary carrier body 44. The carrier body 44 includes an outer surface 46 which is adapted to engage the discrete parts 26 and an opposite, inner surface (not shown) for engaging the carrier base 18 (FIG. 1). The outer surface 46 of the carrier body 44 includes a top surface 48 and a recessed portion 50. The recessed surface 50 is spaced inwardly from the top surface 48 and is connected with the top surface 48 by a connecting wall 52 which defines a height difference H between the recessed portion 50 and the top surface 48. In the embodiment shown, the height difference H is constant along the entire connecting wall 52, however, in alternate embodiments, the height difference H may vary along the connecting wall 52. Furthermore, although the wall 52 is shown as extending substantially normal to the outer surface 48, in alternate embodiments, the wall 52 could be angled, or tapered relative to the outer surface 48. Either or both of the top surface 48 and the recessed portion 50 are preferably curved, and more preferably, both the top surface 48 and the recessed portion 50 have a convex profile in the width direction.

The outer surface 46 of the carrier body 44 preferably includes a plurality of apertures. In the embodiment shown in FIG. 5A, the apertures are located at several locations of the carrier body 44. The top surface 48 includes apertures 54 which extend through the thickness of the carrier body 44 in a direction generally normal to the carrier body 44. The apertures 54 are located and spaced generally along the length of the top surface 48. The top surface 48 also includes angled apertures 56 located generally adjacent the first and second ends 58, 60 of the carrier body 44. The apertures 56 pass through the thickness of the carrier body 44 generally in a direction at an angle to the outer surface 46. The recessed portion 50 also includes larger apertures 62 and 64 which are located substantially inward from the end portions 58, 60, and pass through the thickness of the carrier body generally normal to the outer surface 46. The apertures 62 and 64 are connected by a channel extension 66 which extends along a portion of the length of the recessed portion 50, but does not completely pass through the thickness of the carrier body 44. The recessed portion 50 also includes angled corner apertures 68, which extend through the thickness of the carrier body 44 at an angle to the outer surface 46. The corner apertures 68 are in communication with channel extensions 70, which extend into the connecting wall 52 and the top surface 48, but do not entirely penetrate the thickness of the carrier body 44.

The apertures 64 are preferably used to secure the carrier body 44 to the carrier base 18 by any conventional fastening members, such as bolts (not shown). The other apertures 54, 56, 62, 68 connect to a vacuum plenum (not shown) formed by the carrier body 44 and the carrier base 18 (FIG. 1), and which is in communication with a vacuum source (not shown). The apertures 54, 56, 62, 68, as well as the channel extensions 66, 70, allow for a vacuum pull on the discrete parts 26 (FIG. 1) to secure the discrete parts 26 to the carrier member 20. If vacuum is used, typically only a relatively small amount of vacuum is needed to assist the outer surface 46 of the carrier member 20 to maintain the discrete parts 26 on the outer surface 46. For example, typically no more than about 20 inches of water and desirably only from about 0.1 to about 10 inches of water are required to assist the outer surface 46. The vacuum may be drawn through the apertures in the outer surface 46 by one or more sources of vacuum using conventional techniques for drawing a vacuum as are known to those skilled in the art. The vacuum to each transfer assembly 12 may also be controlled such that a vacuum is only being drawn from the outer surface 46 of each transfer assembly for the period of its rotation when the discrete parts 26 are located on the outer surface 46. For example, the vacuum may be activated just prior to the discrete parts 26 being received and inactivated immediately after the discrete parts 26 are applied to the substrate web 24.

Those skilled in the art will appreciate that other arrays of vacuum apertures may also be used with the present invention. Furthermore, in another embodiment, the vacuum apertures may also be used to apply a blow-off pressure to force the discrete part 26 towards the substrate web 24 (FIG. 1). In other embodiments, there are no vacuum apertures on the carrier member 44, rather, the discrete parts 26 are held on the carrier member 44 simply by the surface roughness of the carrier member 44. In the still other embodiments, the web conveyor 14 (FIG. 1) may include apertures to assist in the transfer of the discrete 26 from the carrier member 44 to the substrate web 24.

In the preferred embodiment of the transfer assembly 12 shown in FIGS. 1 and 5A, the outer surface 46 of the carrier member 20 is curved with a convex profile. Because the web conveyor 14 shown in this embodiment is a rotary drum, the convex shape of the outer surface 46 cooperates with the web conveyor 14 to provide a smooth and accurate transition of the discrete part 26 as it passes from the carrier member 20 to the web conveyor 14.

The recessed portion 50 of the carrier body 44 is dimensioned and configured to accommodate the portion 38 (FIG. 3) of the discrete part 26 that is thicker relative to other portions 40 of the discrete parts. In the example shown in FIG. 5A, the recessed portion 50 is shaped to receive the portion of the discrete part 26 that includes the absorbent layer 36, while the top surface 48 is generally shaped to engage the remaining portions. By accommodating the varying thickness and three-dimensional aspects of the discrete part 26, a better transition of the discrete part 26 to the substrate web 24 is achieved.

More specifically, by contouring the carrier body 44 to account for the thickness and three-dimensional shape of the discrete part 26, a consistent gap is maintained between the discrete part 26 and the substrate web 24 as the transfer assembly 12 passes through its curvilinear path. As a result, the discrete part 26 is more uniformly attached across its width to the substrate web 24, as opposed to only being attached at its thickest portion as would occur in the absence of such contouring. In one embodiment, the transfer assembly 12, the recessed portion 50, and the web conveyor 14 are configured and spaced such that at least 80% of a surface of the discrete part 26 contacts an opposing surface of the substrate web 24 during the rotation of the transfer assembly 12. More, preferably, the transfer assembly 12, the recessed portion 50, and the web conveyor 14 are configured and spaced such that at least 90%, and even more preferably, about 95%, of a surface of the discrete part 26 contacts an opposing surface of the substrate web 24 during the rotation of the transfer assembly 12.

Not only does the uniform contact and attachment provide an improved product, but it can also prevent a buildup of exposed adhesive, thereby improving the reliability of the transport apparatus 10. Moreover, by providing a more consistent gap between the web conveyor 14 and the discrete part 26, it has been found that the gap distance itself may be increased, thereby increasing the positioning tolerance of the process equipment. Furthermore, the thicker portions of the discrete part 26 are protected from compression and possible damage that might occur without the use of a constant gap.

Figure 5B:
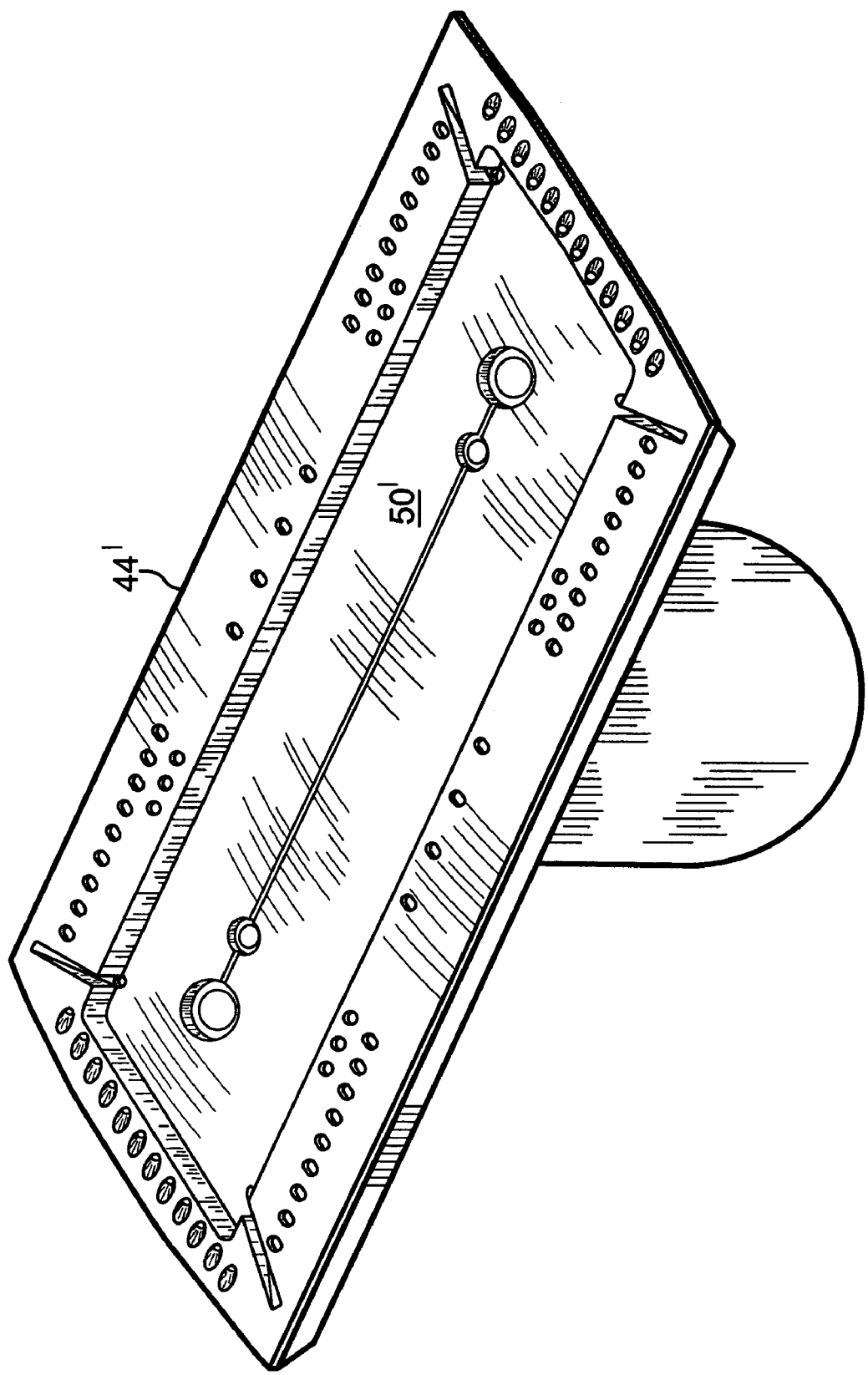
FIG. 5B is a perspective view of another embodiment of a transfer assembly.

The recessed portion 50 shown in FIG. 5A is shaped to receive the portion 38 of the discrete part 26 having absorbent layer 36 (FIG. 2), which is the thickest portion of the discrete part 26. Accordingly, in the example shown, the recessed portion 50 is generally hour-glass shaped, that is, it is generally wider at its end portions 72, 74 than at its central portion 76, to conform to generally hour-glass shape of the absorbent layer 36. Those skilled in the art will recognize that in alternate embodiments the recessed portion 50 can take any shape that is required to engage the contours and varying thicknesses of other discrete parts that may be used in conjunction with the present invention. For example, in one alternate embodiment shown in FIG. 5B, a carrier member 44' has a recessed portion 50' shaped as a rectangle to accommodate a relatively thicker portion of a discrete part that is rectangular. In another example, the recessed portion may have a more circular shape, or a oval shape. In another embodiment where the discrete part 26 has more than two different thicknesses, for example, the recessed portion 50 may be multi-tiered, that is, it may have an intermediate recessed portion with one height difference H and a relatively deeper recessed portion with a greater height difference H.

Referring again to the embodiment shown in FIG. 5A, the first and second ends 58, 60 of the carrier body 50 are at the same height as the top portion 48. However, in alternate embodiments, the ends 58, 60 may be lowered to the height of the recessed portion 50 in order to facilitate the transfer of the discrete part 26 to the transfer assembly 12. Accordingly, the outer surface 46, while substantially following the contouring of the discrete part 26, may include at least some slight deviations from an exact match to the contours of the discrete part in order to facilitate other important functions of the apparatus.

Those skilled in the art will appreciate that the overall dimensions of the carrier body will depend on the discrete part 26 to be processed. The carrier body 44 is preferably made from a lightweight, durable material such as aluminum. The carrier base 18 is preferably made from a lightweight, non-metallic material such as a phenolic composite or any plastic. In a particular aspect, the outer surface 46 of the carrier member 20 may be textured to define a surface roughness which assists in gripping and maintaining the discrete parts 26 on the outer surface 46. As used herein, the term "surface roughness" is the surface roughness of a material as determined by conventional methods known to those skilled in the art. One such method utilizes a profilometer to detect the surface roughness. The stylus of the profilometer is drawn across the textured surface a distance of 1.27 centimeters. The profilometer measures the number of peaks and valleys on the surface as well as the magnitude of each. The profilometer automatically calculates the surface roughness as a Roughness Average ($R_s$) which is the arithmetic average of the measured profile height deviations taken within the sampling length and measured from the graphical centerline. The outer surface 46 of the carrier member 20 may define a surface roughness of at least about 3 micrometers, desirably at least about 10 micrometers and more desirably at least about 15 micrometers. For example, the outer surface 46 may have a surface roughness of from about 5 to about 50 micrometers and desirably from about 10 to about 20 micrometers.

To achieve the surface roughness, the outer surface 46 of each transfer assembly may also include a coating such as a plasma coating. A particularly preferred plasma coating is Plasma Coat PC-902-KC, manufactured and sold by Plasma Coatings of MN, Inc., having an office at 150 West 88th St., Bloomington, Minn. 55420. In a particular aspect wherein the discrete parts 26 being received and applied by the carrier member 20 are elongated elastic parts, it is desirable that the outer surface 46 have a plasma coating which defines a surface roughness of at least about 5 micrometers.

Figure 6:
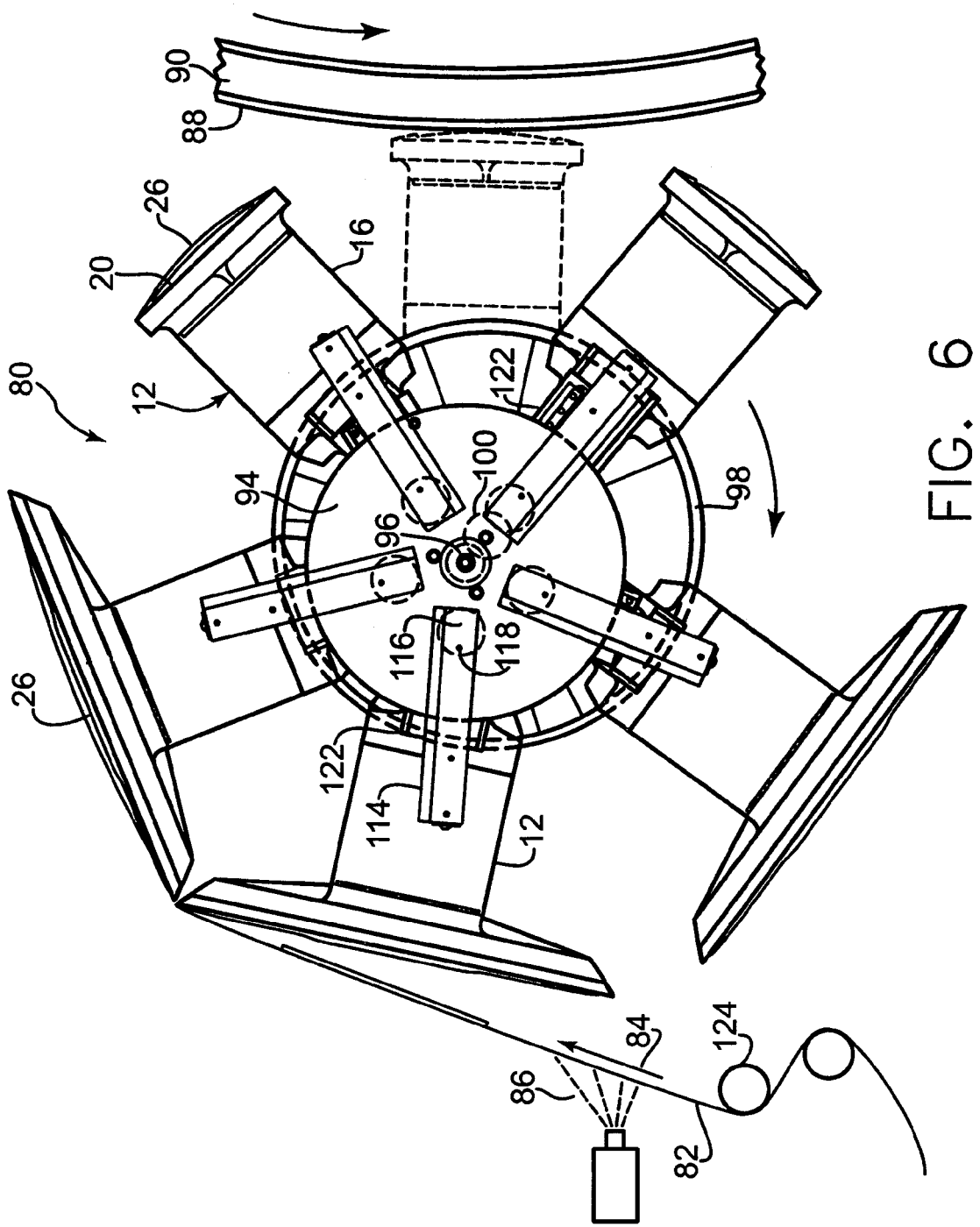
FIG. 6 is a front view of a transport apparatus in accordance with another aspect of the present invention.
Figure 7:
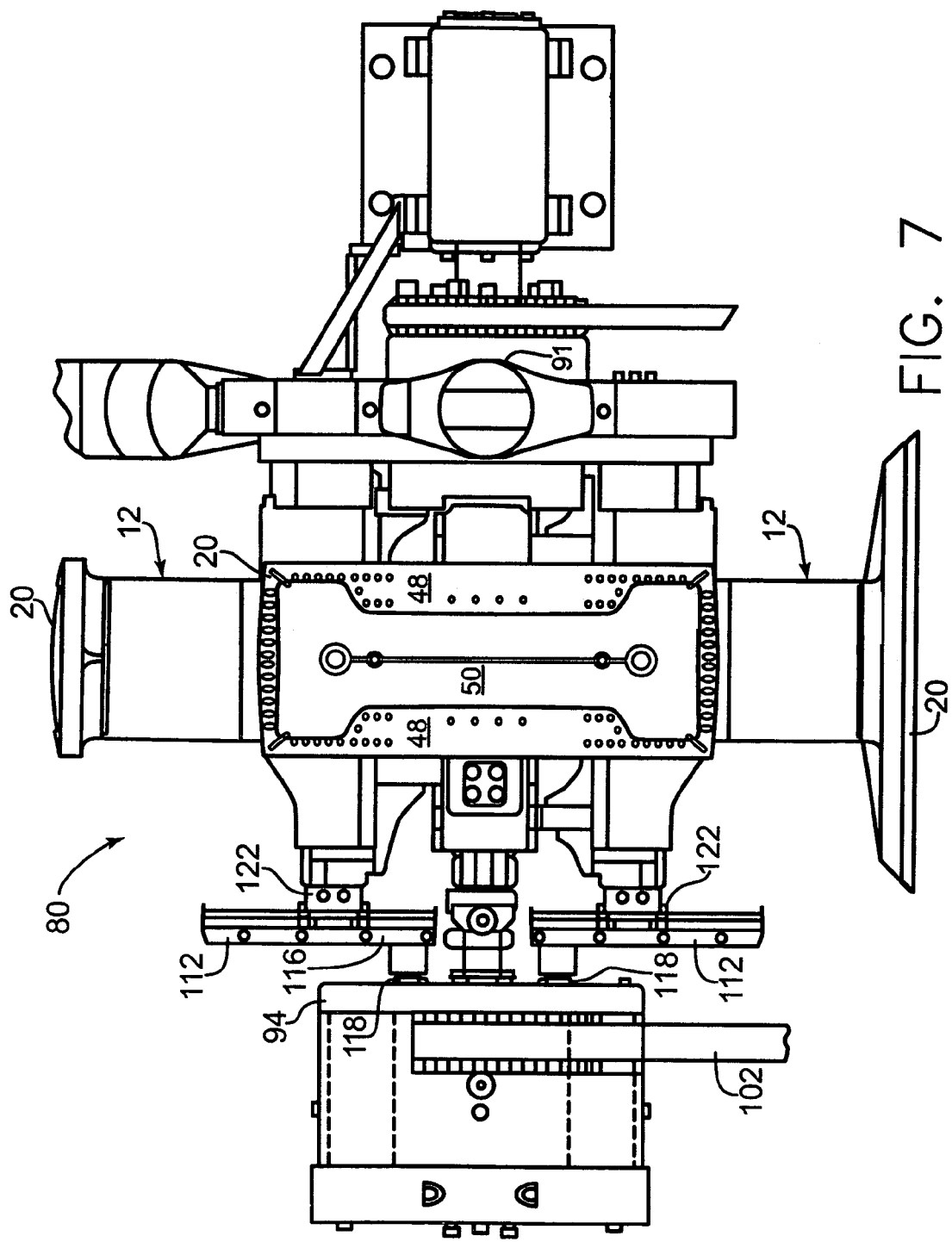
FIG. 7 is a top view of the transport apparatus of FIG. 6.
Figure 8:
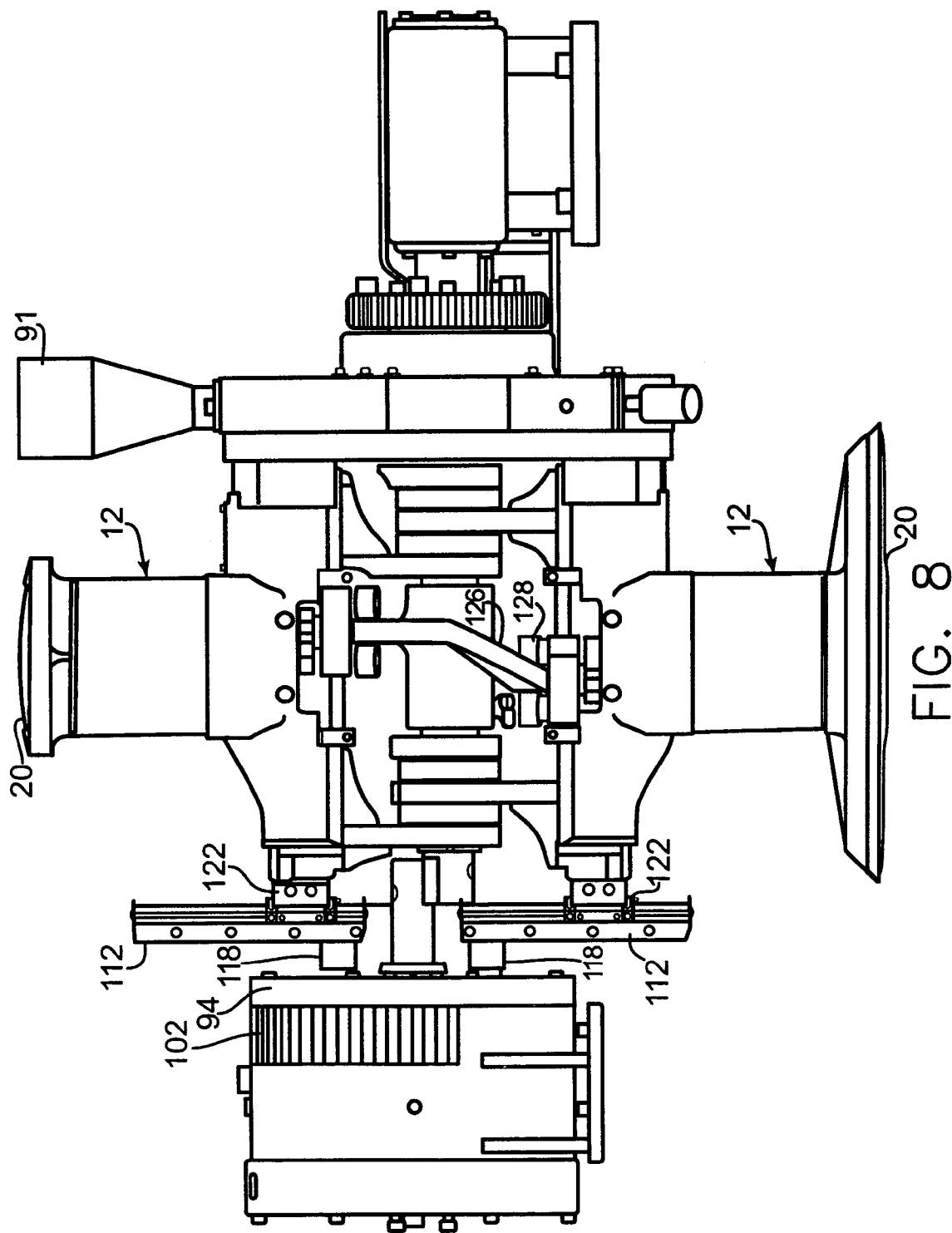
FIG. 8 is a side view of the transport apparatus of FIG. 6.

Referring now to FIGS. 6-8, there is representatively shown one embodiment of a transport apparatus 80 in accordance with the present invention. The illustrated example of the apparatus 80 comprises five transfer assemblies 12 which are configured to transport and apply discrete parts to a substrate web. It should be readily understood that the apparatus 80 may include any number of transfer assemblies 12 depending upon the different web speeds and desired placement and size of the discrete parts. The transport apparatus 80 receives a first web 82 having a plurality of interconnected discrete parts 26, and traveling at a first speed in the direction indicated by the arrow 84 associated therewith. An adhesive 86 is applied to a surface of the first web 82. The movement of the transfer assemblies 12 severs the first substrate web 82 along perforations (not shown) into discrete parts 26 and applies the discrete parts 26 to a substrate web 88 supported by a web conveyor 90, and traveling at a second speed in the direction indicated by the arrow associated therewith. One or more vacuum sources 91 (FIGS. 7-8) are used to provide vacuum to the apertures of the carrier transfer assembly (FIG. 5A) and assist in the transport and transfer of the discrete parts 26 to the second web 88. Each transfer assembly 12 is configured to be moved by a drive member 94 having a first axis 96 such that the surface speed of each transfer assembly 12 is substantially equal to the speed of the first substrate web 82 as the discrete parts 26 are received by the transfer assembly 12 and substantially equal to the speed of the second substrate web 88 as the discrete parts 26 are applied to the substrate web 88, as more fully explained below.

As representatively illustrated in FIGS. 6-8, each transfer assembly 12 is coaxially supported and rotatably connected to a common idler member 98 on a second axis 100. The transfer assemblies 12 are configured to rotate about the second axis 100. Each transfer assembly 12 includes a support member 16 which is rotatably connected to the idler member 98 such that each transfer assembly 12 can be rotated independently. The radial inner end of the support member 16 of each transfer assembly 12 may be rotatably connected to the idler member 98 by any technique known to those skilled in the art such as, for example, using conventional bearings. Similarly, the other components of the transport apparatus 80 of the present invention can be rotatably connected together employing such conventional techniques.

The carrier member 20 of each transfer assembly 12 travels along and defines a common circumferential path that allows the discrete parts 26 to be received form the web 82 and applied to the second substrate web 88. Each carrier member 20 is configured to receive at least one discrete part 26 and apply the discrete part 26 to the second substrate web 88 during each revolution.

The drive member 94 which is configured to move each transfer assembly 12 at a variable speed, but the drive member 94 itself is configured to be rotated at a constant speed about its axis by a driving mechanism 102 (FIG. 7). The driving mechanism 102 may include a motor operatively connected through suitable gearing and drive belts to the drive member 94. Thus, in use, the motor rotates the drive member 94, which, in turn, moves the transfer assemblies 12 at the desired variable speed.

To provide the desired variable speed of each transfer assembly 12, the axis 96 of the drive member 94 is offset from the axis 100 of the idler member 98 and the transfer assemblies 12 by an offset distance. The offset distance between the first axis 96 and the second axis 100 may be any distance which provides the desired variations in the speed of the outer surface 46 of each transfer assembly 12.

The apparatus 80 further includes at least one coupler arm 112 which has a first end portion 114 and a second end portion 116. The second end portion 116 is pivotally connected to the drive member 94 about a pivot point 118. The apparatus 80 typically includes one coupler arm 112 for each transfer assembly 12. Accordingly, in the apparatus 80 representatively illustrated in FIGS. 6-8 which includes five transfer assemblies 12, five coupler arms 112 independently connect the drive member 94 to each respective transfer assembly 12. The coupler arms 112 are pivotally connected to the drive member 94 about pivot points 118 which are selectively located to provide the desired speeds for the transfer assemblies 12. In a particular aspect, the pivot points 118 for the coupler arms 112 are located the same distance radially outward from the axis 96 of the drive member 94. In such a configuration, the pivot points 118 rotate at a constant speed along a common circumferential path as the drive member 94 is rotated at a constant speed. The coupler arms 112 may be pivotally connected to the drive member 94 by conventional means known to those skilled in the art.

The coupler arm 112 is configured to follow a curvilinear path and is slidably connected to a respective transfer assembly 12. As the drive member 94 is rotated, the coupler arm 112 is guided along the curvilinear path and each coupler arm slidably engages the respective transfer assembly 12 thereby pivoting the coupler arm 112 about the pivot point 118. The pivoting of the coupler arm 112 and the offset crank motion of the drive member 94 vary the effective drive radius of each transfer assembly 12 and move each transfer assembly 12 at a variable speed. The second end portion 116 of each coupler arm 112 may be slidably connected to the respective transfer assembly 12 by any means known to those skilled in the art, such as by a slide track 122.

The use of the combination of the offset drive member 94 and pivoting coupler arm 112 to drive the transfer assemblies 12 in the apparatus 80, as representatively illustrated in the various aspects of the invention described above, provides an inexpensive and adaptable method for severing a first substrate web 82 traveling at a speed into discrete parts 26 and applying the discrete parts 26 to a substrate web 88 traveling at a different speed. The design of the drive member 94 and coupler arm 112 can be analytically determined to obtain the desired output function which can include variable angular velocities with fixed speed dwells.

In a particular aspect, the surface speed of each transfer assembly 12 is maintained substantially constant as the discrete parts 26 are received from the feed conveyor 124. The surface speed may be variable while the transfer assembly is rotated 90 degrees prior to the application of the discrete part unto the substrate web 88. The surface speed is constant when the discrete part is applied to the substrate web 88.

The apparatus and method of the present invention may be used in the manufacture of discrete parts such as diapers, training pants, and adult incontinence products, among other uses. In particular, the apparatus and method may be used to apply discrete parts or components, such as, for example, absorbent layers, waist elastics, leg elastics, tapes, snaps, and hook and loop materials to the diaper or incontinence product. Discrete parts such as diapers and incontinence products are described, for example, in U.S. Pat. Nos. 4,704,116 issued Nov. 3, 1987, to Enloe; U.S. Pat. No. 4,798,603 issued Jan. 17, 1989, to Meyer et al.; U.S. Pat. No. 4,710,187 issued Dec. 1, 1987, to Boland et al.; U.S. Pat. No. 4,770,656 issued Sep. 13, 1988, to Proxmire et al.; and U.S. Pat. No. 4,762,521 issued Aug. 9, 1988 to Roessler et al., and commonly assigned, copending U.S. app. Ser. No. 09/825,609, entitled "Absorbent Insert For Use With An Outer Absorbent Garment," filed Apr. 3, 2001; the disclosures of which are incorporated by reference.

As representatively illustrated in FIG. 8, the apparatus 80 may further include a turning mechanism 126 and a follower 128 for rotating the transfer assemblies 12 before they apply the discrete parts 26 to the second substrate web 88. Any mechanism which provides the desired rotation of the transfer assemblies 12 can be used. For example, one suitable mechanism is a barrel cam as is well known to those skilled in the art. Thus, in use, the discrete parts 26 may be received by the transfer assembly 12 while oriented in one direction and, subsequently, be rotated by the turning mechanism 126 and the follower 128 before being applied to the second substrate web 88. The turning mechanism 126 can be configured to rotate the transfer assemblies 12 any amount. For example, the turning mechanism 126 may be configured to rotate the transfer assemblies 12 from about 1 to about 180 degrees and desirably from about 1 to about 90 degrees before they are applied depending upon the desired orientation of the parts 26 on the second substrate web 88.

Figure 9:
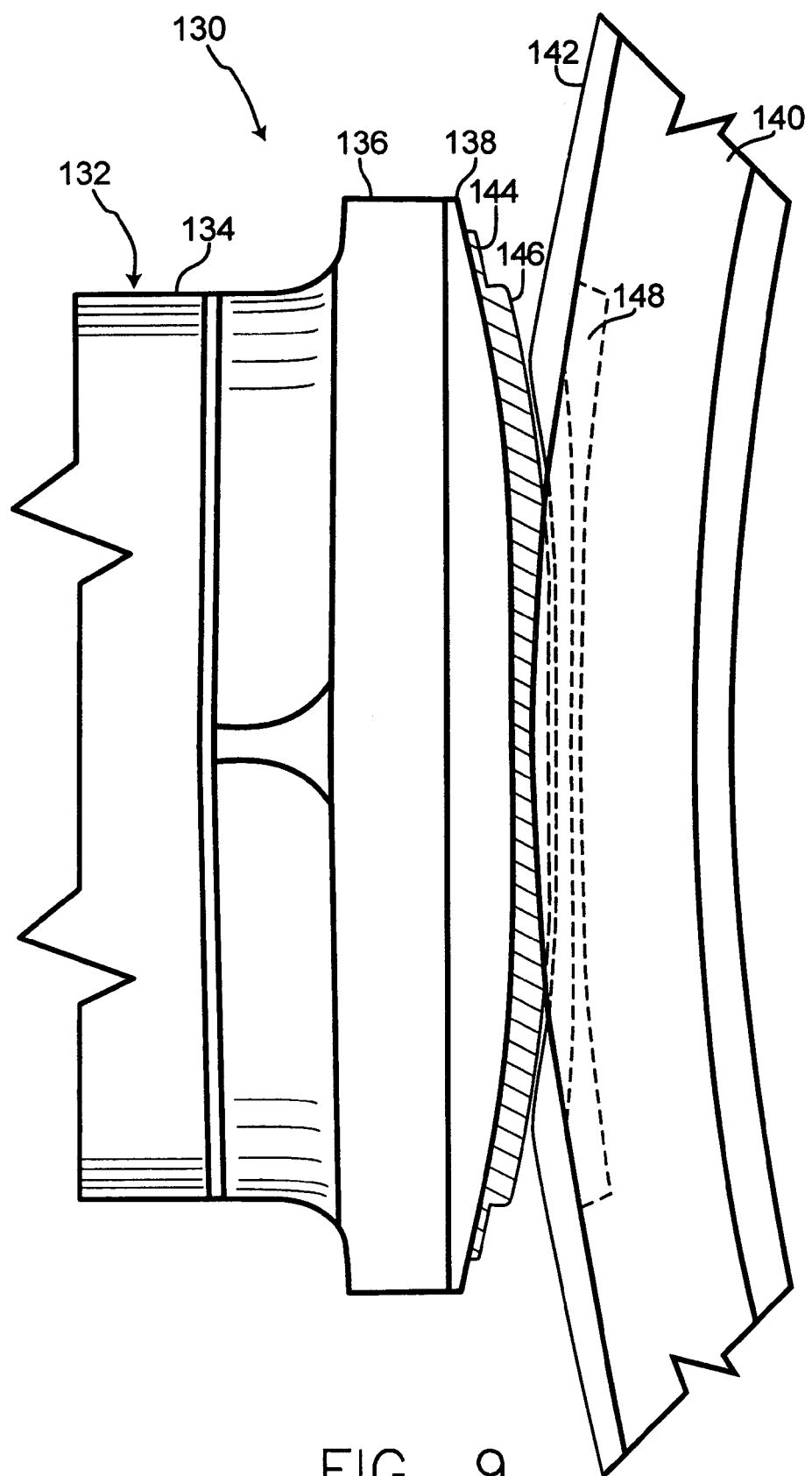
FIG. 9 is a front view of another embodiment of a transport apparatus according to the invention.

Turning now to FIG. 9, an alternate embodiment of a transport apparatus is shown generally at 130. The transport apparatus 130 includes a transfer assembly 132 having a support member 134, a carrier base 136, and a carrier member 138. Like the previous embodiments, the transfer assembly 132 is adapted to rotate about an axis (not shown) by an appropriate drive member (not shown). The transfer assembly 132 is spaced from a web conveyor 140, which supports and advances a substrate web 142. The carrier member 138 is adapted to engage a discrete part 144 having a relatively thicker portion 146, and transfer the discrete part 144 to the substrate web 142, just as in the other embodiments described above. However, in this embodiment, the carrier member 138 does not include a recessed portion. Rather, the web conveyor 140 includes a recessed portion 148 that is generally shaped and contoured to accommodate the relatively thicker portion 146 of the discrete part 144.

While the invention has been described in detail with respect to specific aspects thereof, it will be appreciated that those skilled in the art, upon attaining an understanding of the foregoing, may readily conceive of alterations to, variations of, and equivalents to these aspects. For example, it will be apparent that the continuously moving substrate web 82, in certain aspects of the invention, may be omitted and the discrete parts 26 may be placed directly upon each transfer assembly 12. In addition, it will be apparent that the discrete parts 26 may be adhered to the second substrate web 88 by means of an adhesive applied in a selected pattern to the surface of the discrete parts 26, or by any other suitable means for adhering the discrete parts 26 to the substrate web 88. Accordingly, the scope of the present invention should be assessed as that of the appended claims and any equivalents thereto.

The invention claimed is:

1. A transfer assembly for transporting and applying a discrete part to a moving web, the discrete part having varying thickness, the transfer assembly comprising:
   a carrier body having a discrete part engaging outer surface, the outer surface including a generally convex top portion and a generally convex recessed portion spaced inwardly from said top portion, wherein said recessed portion has a fixed, non-changeable hour-glass shape, and wherein said carrier body is rotatable about an axis substantially normal to a bottom surface of said recessed portion; said top portion adapted and configured to engage a first portion of a discrete part having a first thickness, said recessed portion adapted and configured to engage at least one portion of the discrete part having at least one thickness greater than said first thickness, and further comprising at least one aperture in said outer surface and extending through said carrier body for communication with a vacuum source.

2. The transfer assembly of claim 1, wherein said recessed portion is located generally centrally in said outer surface.

3. The transfer assembly of claim 1 further comprising a carrier base adapted to support said carrier body.

4. The transfer assembly of claim 1 wherein said outer surface has a surface roughness of at least 3 micrometers.

5. The transfer assembly of claim 1 wherein said outer surface includes a plasma coating thereon.

6. An apparatus for applying discrete parts traveling at a first speed and having a varying thickness onto a substrate web traveling at a second speed, said apparatus comprising:
   a) a web conveyor adapted to support and advance said substrate web;

b) at least one transfer assembly configured to rotate about a first axis, said transfer assembly including an outer surface which is configured to transport said discrete parts and apply said discrete parts to said substrate web; said outer surface including at least one generally convex recessed portion having a generally convex bottom surface for engaging at least one portion of the discrete parts that is relatively thicker than other portions of the discrete parts;

c) a drive member which is configured to rotate about a second axis which is offset from said first axis of said transfer assembly;

d) at least one coupler arm which is pivotally connected to said drive member about a pivot point, said coupler arm including a cam end which is configured to follow a curvilinear path and a crank end which is slidably connected to said transfer assembly; and e) a drive mechanism adapted to rotate said drive member about said second axis wherein, as said drive member is rotated, said cam end of said coupler arm is guided along said curvilinear path and said crank end of said coupler arm slidably engages said transfer assembly thereby pivoting said coupler arm about said pivot point to vary an effective drive radius of said transfer assembly and rotate said transfer assembly at a variable speed.

7. The apparatus of claim 6 wherein said transfer assembly is configured to maintain a substantially constant first surface speed as the discrete parts are received and a substantially constant second surface speed as the discrete parts are applied to said substrate web.

8. The apparatus of claim 6 wherein said first surface speed of said transfer assembly is substantially equal to said first speed of said discrete parts and said second surface speed of said transfer assembly is substantially equal to said second speed of said substrate web.

9. The apparatus of claim 6, further comprising a turning mechanism adapted to rotate said at least one transfer assembly before the discrete parts are applied to said substrate web.

10. A transfer assembly for transporting and applying a discrete part to a moving web, the discrete part having varying thickness, the transfer assembly comprising:

a carrier body having a discrete part engaging outer surface, the outer surface including a generally convex top portion and a generally convex recessed portion spaced inwardly from said top portion; said top portion adapted and configured to engage a first portion of a discrete part having a first thickness, said recessed portion having a bottom surface adapted and configured to engage at least one portion of the discrete part having at least one thickness greater than said first thickness; said bottom surface of said recessed portion having a first predetermined shape relative to said top portion and said top portion having a second predetermined shape relative to said recessed portion when said bottom surface of said recessed portion and said top portion are viewed along an axis substantially normal to said bottom surface of said recessed portion, and further comprising at least one aperture in said top portion of said outer surface and extending through said carrier body for communication with a vacuum source, wherein said carrier body is rotatable about said axis substantially normal to said bottom surface of said recessed portion, and wherein said first predetermined shape of said bottom surface of said recessed portion and said second predetermined shape of said top portion remain fixed as carrier body is rotated about said axis.

11. The transfer assembly of claim 1 wherein said at least one aperture is formed in said top portion of said outer surface and extends through said carrier body for communication with said vacuum source.

12. The transfer assembly of claim 1 wherein said at least one aperture is formed in said recessed portion of said outer surface and extends through said carrier body for communication with said vacuum source.

13. The transfer assembly of claim 1 wherein said top portion and said recessed portions are integrally formed as a single unitary component.

14. The transfer assembly of claim 10 further comprising at least one aperture in said recessed portion of said outer surface and extending through said carrier body for communication with said vacuum source.

15. The transfer assembly of claim 10 wherein said top portion and said recessed portions are integrally formed as a single unitary component.

16. The transfer assembly of claim 10, wherein said recessed portion is located generally centrally in said outer surface.

17. The transfer assembly of claim 10 further comprising a carrier base adapted to support said carrier body.

18. The transfer assembly of claim 10 wherein said outer surface has a surface roughness of at least 3 micrometers.

19. The transfer assembly of claim 10 wherein said outer surface includes a plasma coating thereon.

* * * * *